(12) United States Patent
Casas (10) Patent No.: US 10,786,612 B2
(45) Date of Patent: *Sep. 29, 2020

(54) INSTRUMENTED DRIVELINE USING A FLEXIBLE ARTIFICIAL SKIN SENSORY ARRAY

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 61 days.

This patent is subject to a terminal disclaimer.

(21) Appl. No.: 16/131,238

(22) Filed: Sep. 14, 2018

(65) Prior Publication Data

US 2019/0091390 A1 Mar. 28, 2019

Related U.S. Application Data

(60) Provisional application No. 62/563,333, filed on Sep. 26, 2017.

(51) Int. Cl.
*A61M 1/10* (2006.01)
*A61M 1/12* (2006.01)

(52) U.S. Cl.
CPC ........ *A61M 1/1086* (2013.01); *A61M 1/1008* (2014.02); *A61M 1/12* (2013.01); *A61M 1/122* (2014.02); *A61M 1/127* (2013.01); *A61M 2205/3327* (2013.01); *A61M 2205/3592* (2013.01); *A61M 2230/62* (2013.01); *A61M 2230/63* (2013.01)

(58) Field of Classification Search
CPC ........................... A61M 1/1086; A61M 1/127
See application file for complete search history.

(56) References Cited

U.S. PATENT DOCUMENTS

| 2004/0167563 | A1 | 8/2004 | Fogarty et al. |
| 2004/0267086 | A1 | 12/2004 | Anstadt et al. |
| 2006/0030747 | A1 | 2/2006 | Kantrowitz et al. |
| 2008/0045779 | A1 | 2/2008 | Rinaldi et al. |

(Continued)

FOREIGN PATENT DOCUMENTS

WO 2015034955 A1 3/2015

OTHER PUBLICATIONS

International Search Report and Written Opinion dated Nov. 22, 2018, for corresponding International Application No. PCT/US2018/051013; International Filing Date: Sep. 14, 2018 consisting of 12-pages.

*Primary Examiner* — Gary Jackson
*Assistant Examiner* — Zahed Kabir
(74) *Attorney, Agent, or Firm* — Christopher & Weisberg, P.A.

(57) ABSTRACT

A driveline for an implantable blood pump including a percutaneous connector including an outer tube, the outer tube defining an exterior surface and having a proximal portion and a distal portion opposite the proximal portion, the proximal portion being couplable to the implantable blood pump disposed within a body of a patient and the distal portion being couplable to a controller outside of the body of the patient and at least one electronic instrument coupled to the outer tube and fluidically sealed from the exterior surface.

17 Claims, 6 Drawing Sheets

(56) References Cited

U.S. PATENT DOCUMENTS

| | | | |
|---|---|---|---|
| 2009/0318757 A1* | 12/2009 | Singh | A61B 1/012 600/109 |
| 2010/0204539 A1* | 8/2010 | Tansley | A61M 1/127 600/17 |
| 2011/0160516 A1* | 6/2011 | Dague | A61M 1/127 600/16 |
| 2012/0203318 A1* | 8/2012 | Mann | A61M 39/0247 607/116 |
| 2013/0104884 A1* | 5/2013 | Vazales | A61M 16/0418 128/202.16 |
| 2015/0258261 A1 | 9/2015 | Novack | |
| 2016/0199556 A1* | 7/2016 | Ayre | A61M 1/101 600/16 |
| 2016/0228061 A1* | 8/2016 | Kallback | A61B 5/6852 |
| 2017/0258981 A1* | 9/2017 | Franano | A61M 5/16831 |
| 2018/0200422 A1* | 7/2018 | Nguyen | A61M 1/127 |
| 2018/0243490 A1* | 8/2018 | Kallenbach | A61M 1/122 |

* cited by examiner

INSTRUMENTED DRIVELINE USING A FLEXIBLE ARTIFICIAL SKIN SENSORY ARRAY

CROSS-REFERENCE TO RELATED APPLICATIONS

This application claims the benefit of U.S. Application Ser. No. 62/563,333, filed Sep. 26, 2017, the entirety of which is incorporated herein by reference.

FIELD

The present technology is generally related to a driveline for an implantable blood pump.

BACKGROUND

A driveline of an implantable blood pump provides power from a power source, such as an external controller, to the blood pump when the blood pump is implanted within a human or animal patient. The driveline is typically formed as an elongate tube containing one or more conductors that percutaneously extend through the patient's skin proximate the abdomen to connect with the blood pump. The purpose of existing drivelines, however, is limited to supplying power to the blood pump.

SUMMARY

The techniques of this disclosure generally relate to a driveline for an implantable blood pump including a percutaneous connector and at least one electronic instrument coupled to the driveline.

In one aspect, the present disclosure provides a driveline for an implantable blood pump including a percutaneous connector having an outer tube, the outer tube defining an exterior surface and including a proximal portion and a distal portion opposite the proximal portion, the proximal portion being couplable to the implantable blood pump disposed within a body of a patient and the distal portion being couplable to an external controller outside of the body of the patient. In addition, the driveline includes at least one electronic instrument coupled to the outer tube and fluidically sealed from the exterior surface of the outer tube.

In another aspect, the disclosure provides the at least one electronic instrument being at least one from a group consisting of a wireless transmitter and a transcutaneous energy transfer receiver.

In another aspect, the disclosure provides the at least one electronic instrument being an activity sensor.

In another aspect, the disclosure provides the activity sensor including an accelerometer in communication with the wireless transmitter, and wherein the wireless transmitter is configured to transmit patient positional information measured by the accelerometer to the external controller.

In another aspect, the disclosure provides the external controller being configured to alter an operation of the implantable blood pump based on the patient positional information measured by the accelerometer.

In another aspect, the disclosure provides the patient positional information including a measure of a movement and an orientation of the body of the patient.

In yet another aspect, the disclosure provides the at least one electronic instrument being a moisture sensor.

In another aspect, the disclosure provides the outer tube defining a lumen including a one or more conductors disposed therein.

In another aspect, the disclosure provides the exterior surface of the outer tube including a biocompatible fabric disposed around at least a portion thereof.

In another aspect, the disclosure provides the biocompatible fabric being a velour material.

In another aspect, the disclosure provides the biocompatible fabric including an interior surface and an exterior surface opposite the interior surface, the interior surface configured to be in contact with the exterior surface of the outer tube and to include the at least one electronic instrument disposed thereon.

In another aspect, the disclosure provides the distal portion of the outer tube extending out from the body of the patient when the connector is implanted in the body of the patient, and the at least one electronic instrument is disposed around the distal portion.

In another aspect, the disclosure provides the at least one electronic instrument being adhered to the connector.

In another aspect, the present disclosure provides a driveline for an implantable blood pump defining a communication channel between the implantable blood pump and an external controller, the driveline including a percutaneous connector having an outer tube, the outer tube defining a proximal portion and a distal portion opposite the proximal portion and an electronic instrument contouring the outer tube and extending proximally along the outer tube.

In another aspect, the outer tube defines a lumen including one or more conductors disposed therein.

In another aspect, the driveline includes a biocompatible fabric including an interior surface and an exterior surface opposite the interior surface, the interior surface of the biocompatible fabric being in contact with the outer tube and including the electronic instrument disposed thereon.

In another aspect, the biocompatible fabric is a velour material.

In another aspect, the electronic instrument is adhered to the connector.

In another aspect, the electronic instrument is at least one from a group consisting of a wireless transmitter, a transcutaneous energy transfer receiver, a moisture sensor, and an activity sensor.

In another aspect, the present disclosure provides a driveline for an implantable blood pump, the driveline including a percutaneous connector and an outer tube coupled to the connector, the outer tube having a proximal portion and a distal portion opposite the proximal portion, the proximal portion being couplable to the implantable blood pump disposed within a body of a patient and the distal portion being couplable to an external controller outside of the body of the patient. The outer tube of the percutaneous connector may define a lumen including a plurality of conductors disposed therein and an exterior surface including a biocompatible fabric in contact therewith at the distal portion of the outer tube, the biocompatible fabric having an interior surface and an exterior surface opposite the interior surface. In addition, at least one electronic instrument is disposed between the interior surface of the biocompatible fabric and the exterior surface of the outer tube.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of device components, system components, and processing steps related to instrumenting a driveline for an implantable blood pump. Accordingly, the device, system, and process components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described processes or methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawings in which like reference designators refer to like elements, there is shown in FIGS. 1-6 an exemplary driveline constructed in accordance with the principles of the present disclosure and designated generally as "10." The driveline 10 may be made of a flexible material that extends a predetermined length from an implanted blood pump coupled to heart of a human or an animal patient percutaneously out of the patient at the abdomen. As such, the driveline 10 is a percutaneous connector configured to connect the implanted blood pump to a device external to the patient, such as an external controller, to define a communication channel between the blood pump and the external controller.

Figure 1:
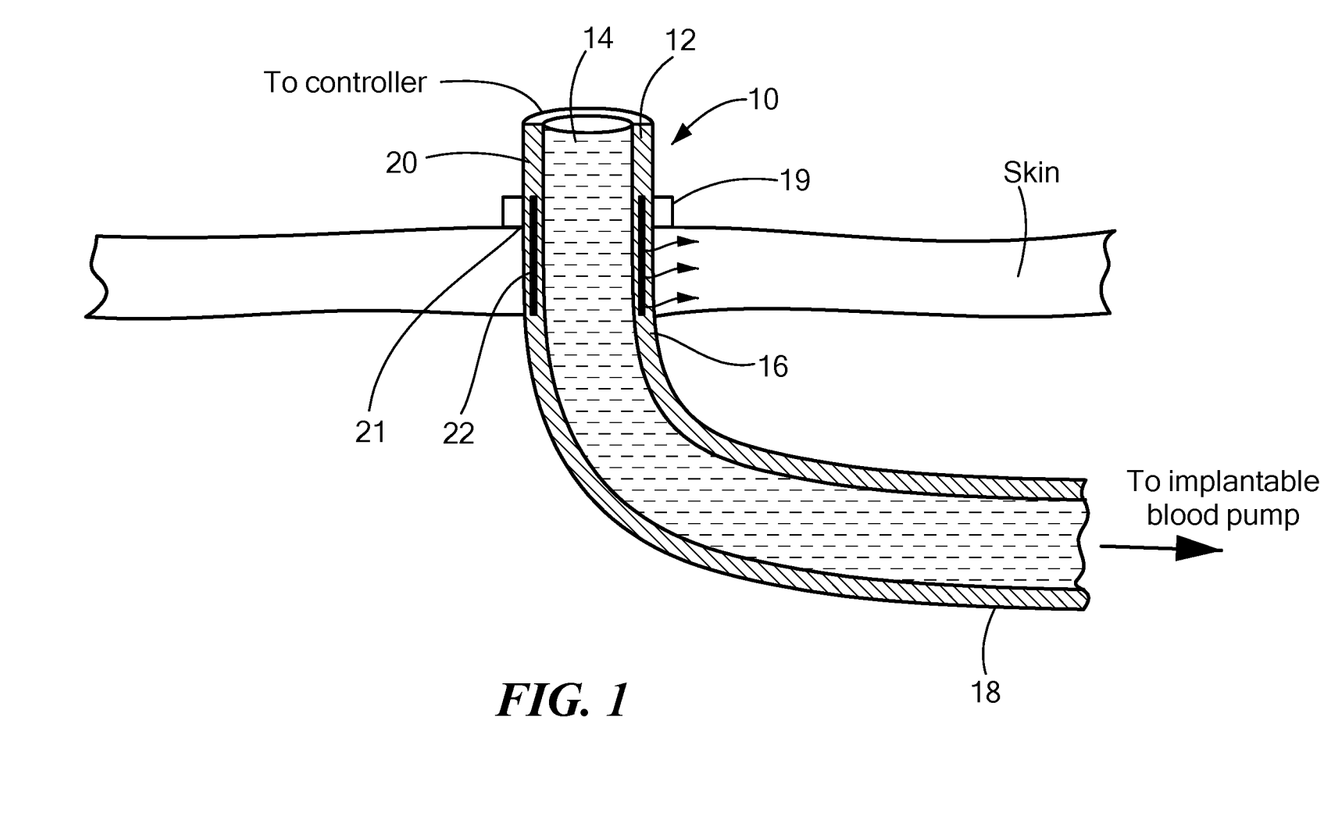
FIG. 1 is a cross-sectional view of an exemplary driveline shown extending through the skin of a patient and connectable to an implantable blood pump, the driveline including a biocompatible fabric and an electronic instrument coupled thereto.
Figure 2:
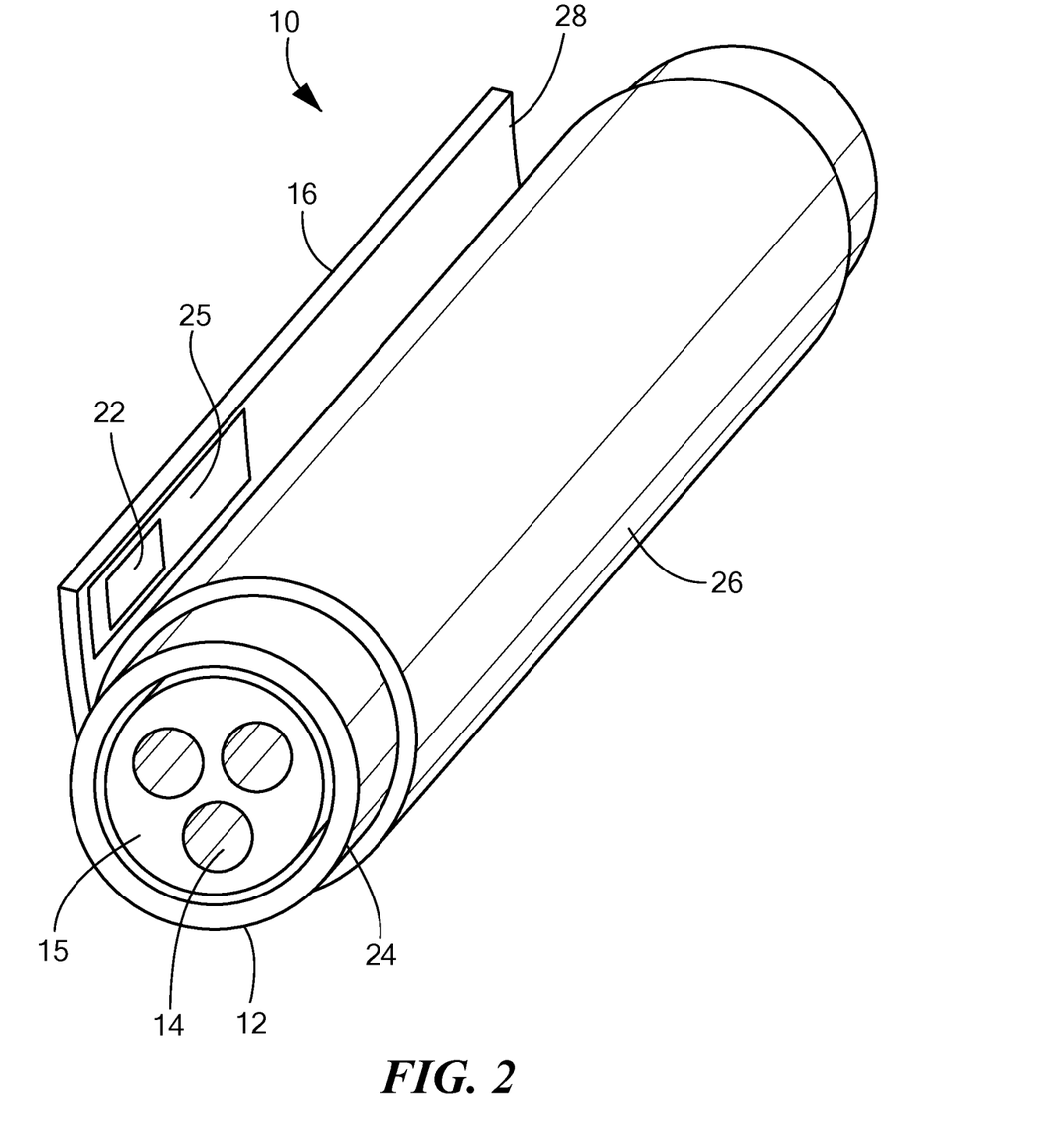
FIG. 2 is a perspective view of the driveline of FIG. 1.

With reference to FIG. 1, the driveline 10, i.e., percutaneous connector, includes an outer tube 12 defining at least one lumen 14 for receiving a conductor therethrough. The outer tube 12 may be composed of a flexible, biocompatible, and water proof material, for example, nylon, braided nylon, or the like, which may incorporate material properties configured to prevent kinking. FIG. 2 depicts the outer tube 12 defining three lumens 14 for receiving corresponding conductors therein, however more or less lumens may be provided. The lumens 14 may further be formed by or disposed within an inner tube 15 that spans all or a majority of the length of the outer tube 12 to insulate the conductors.

The inner tube 15 may be slidable within an inner diameter of the outer tube 12 or otherwise disposed within the outer tube 12.

With reference to FIGS. 1 and 2, a biocompatible fabric 16 may be coupled to the outer tube 12 to promote tissue ingrowth into the driveline 10. In one configuration, the fabric 16 is a velour material. In other configurations, the fabric 16 may be a woven polyester or another fabric that is biocompatible and prone to promoting tissue ingrowth. The fabric 16 may be wrapped around the outer tube 12 and extend the entire length or less than the entire length of the outer tube 12. For example, as shown in FIG. 1, the outer tube 12 defines a proximal portion 18 and a distal portion 20 opposite the proximal portion 18. When the driveline 10 is implanted in the body of the patient, the proximal portion 18 of the outer tube 12 may be connected to an implantable blood pump (not shown) and the distal portion 20 may extend percutaneously to couple to an external controller (not shown) with the fabric 16 being wrapped around or otherwise coupled to only the distal portion 20 of the outer tube 12. In particular, the distal portion 20 includes a first end portion 19 extending out from the body of the patient and the proximal portion 18 includes a second end portion 21 configured to connect to the implantable blood pump, and at least one electronic instrument 22 is disposed around the first end portion 19.

The electronic instrument 22 may be one or more of a wireless transmitter, a transcutaneous energy transfer receiver, an activity sensor, or a moisture sensor, that is permanently or releasably coupled to the driveline 10. For example, the electronic instrument 22 may be printed onto the outer tube 12 through a printing process, coupled to the outer tube 12 using an adhesive, or may be clamped or otherwise mechanically coupled to the outer tube 12. In other configurations, the electronic instrument 22 may be affixed, adhered to, or embedded within the fabric 16. The coupling configurations may be designed to occupy minimal space along the driveline 10. For example, FIG. 1 depicts the fabric 16 contouring the outer tube 12 and the electronic instrument 22 embedded within the fabric 16. With reference to FIG. 2, the outer tube 12 includes an exterior surface 24 which defines the circumference of the outer tube 12 and the fabric 16 may be wrapped around a portion of the circumference including the entire or less than the entire circumference of the connector. In addition, referring still to FIG. 2, the fabric 16 defines an exterior surface 26 and an interior surface 28 opposite the exterior surface. In order to fluidly isolate the electronic instrument 22 from moisture and any body fluids, the electronic instrument 22 may be adhered or otherwise embedded on the interior surface 28. As such, the interior surface 28 of the fabric 16 may overlap the exterior surface 26 of the fabric 16 to fluidically seal the electronic instrument 22 from the exterior surface 24 of the outer tube 12 and thus body fluids.

In one exemplary configuration, the fabric 16 and the electronic instrument 22 may be incorporated as part of a MEMS device 25 coupled to or integrated within the driveline 10. For example, the MEMS device 25 may be a flexible circuit sticker having circuitry configured to receive power and supply such power to the electronic instrument 22. The power may be received by way of passive inductive radiofrequency charging, transcutaneous energy harvesting, a separate transcutaneous energy transfer system, or other methods known in the art. Alternatively, one or more of the conductors disposed within the driveline 10 may be split or a separate conductor may be included in the driveline 10 to power the electronic instrument 22.

Figure 3:
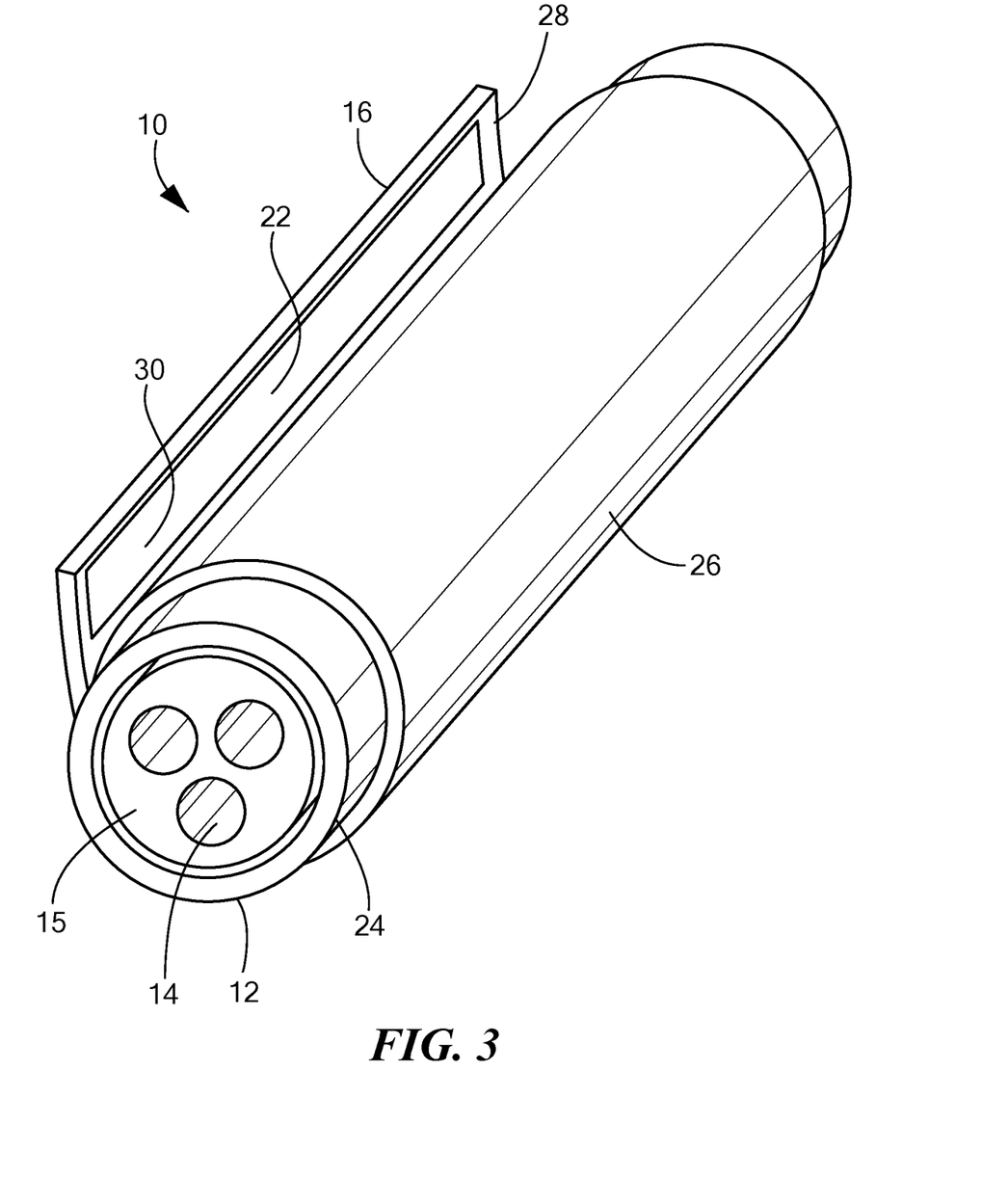
FIG. 3 is a perspective view of the driveline of FIG. 1 showing the electronic instrument as a moisture sensor.

Referring now to FIG. 3, the electronic instrument 22 is shown as a moisture sensor 30 which may be coupled to or embedded within one or more predetermined areas of the fabric 16, the outer tube 12, or the inner tube 15. For example, the fabric 16 may include one or more layers and the moisture sensor 30 may be embedded in the outermost or one of the outermost layers of the fabric 16. As such, moisture penetrating the fabric 16 beyond a predetermined layer can be detected by the moisture sensor 30. When wrapped around the inner tube 15, the moisture sensor 30 may be configured to detect fluid that penetrates the outer tube 12 to prevent short circuits. As with other configurations of the electronic instrument 22, the moisture sensor 30 can span the entire length or select portions of the driveline 10 along the length.

The moisture sensor 30 may be in communication with the external controller when coupled to the blood pump to generate an alert when the driveline 10 may benefit from being repositioned or replaced. The moisture sensor 30 may have its own power source or may harvest power from the driveline 10 by radiofrequency or transcutaneous energy transfer. In the case of transcutaneous energy transfer, the moisture sensor 30 may be part of a MEMS device, such as the MEMS device 25 of FIG. 1, with the MEMS device including a secondary coil positioned thereon.

Figure 4:
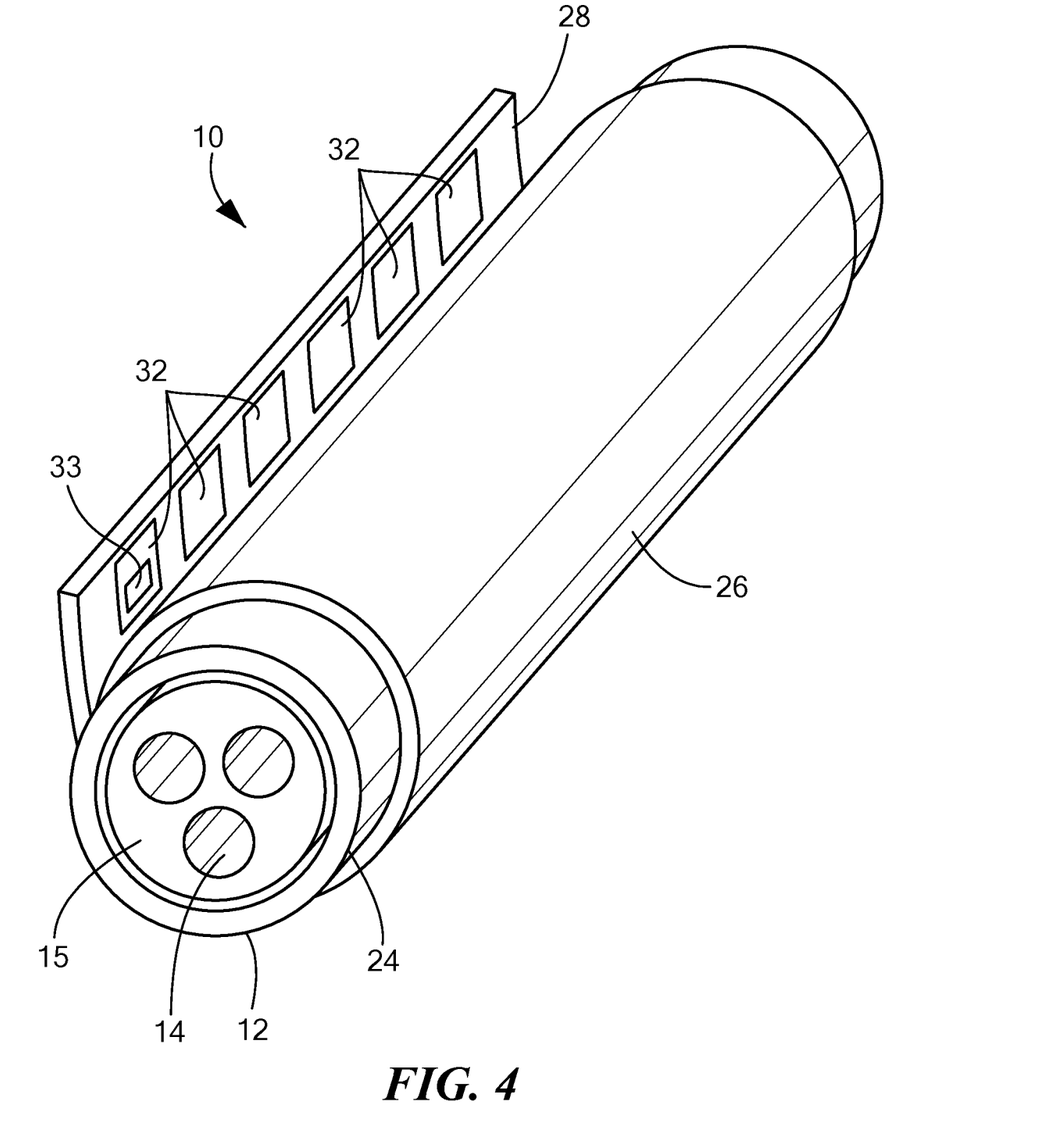
FIG. 4 is a perspective view of the driveline of FIG. 1 showing the electronic instrument as an activity sensor.

Referring now to FIG. 4, the electronic instrument 22 is shown as an activity sensor 32 configured to measure and monitor the position, orientation, and/or movement of the driveline 10 and hence the patient relative to a reference region or area. The activity sensor 32 may include an accelerometer 33 to obtain the measurements and associated measurement information. Such information may be processed in a processor of the electronic instrument 22 or external controller and correlated to determine an activity or position of the patient, such as the patient beginning to walk, ceasing to walk, lying down, standing up, sitting down, etc. The controller may modify the power provided to the blood pump in response to the correlated activity. For example, when the activity sensor 32 determines that the patient is walking, the power to the blood pump may be increased to increase blood flow. Similarly, power to the blood pump may be decreased when the patient is lying down to decrease blood flow.

In one configuration, as shown in FIG. 4, the activity sensor 32 may include an array of independent activity sensors 32 distributed along the entire length or less than the entire length of the driveline 10, such as at the distal portion 20 of the outer tube 12. The independent activity sensors 32 may communicate with each other to detect relatively complex motions that can be correlated by the processor to determine the type of movement or activity, such as exercising.

Figure 5:
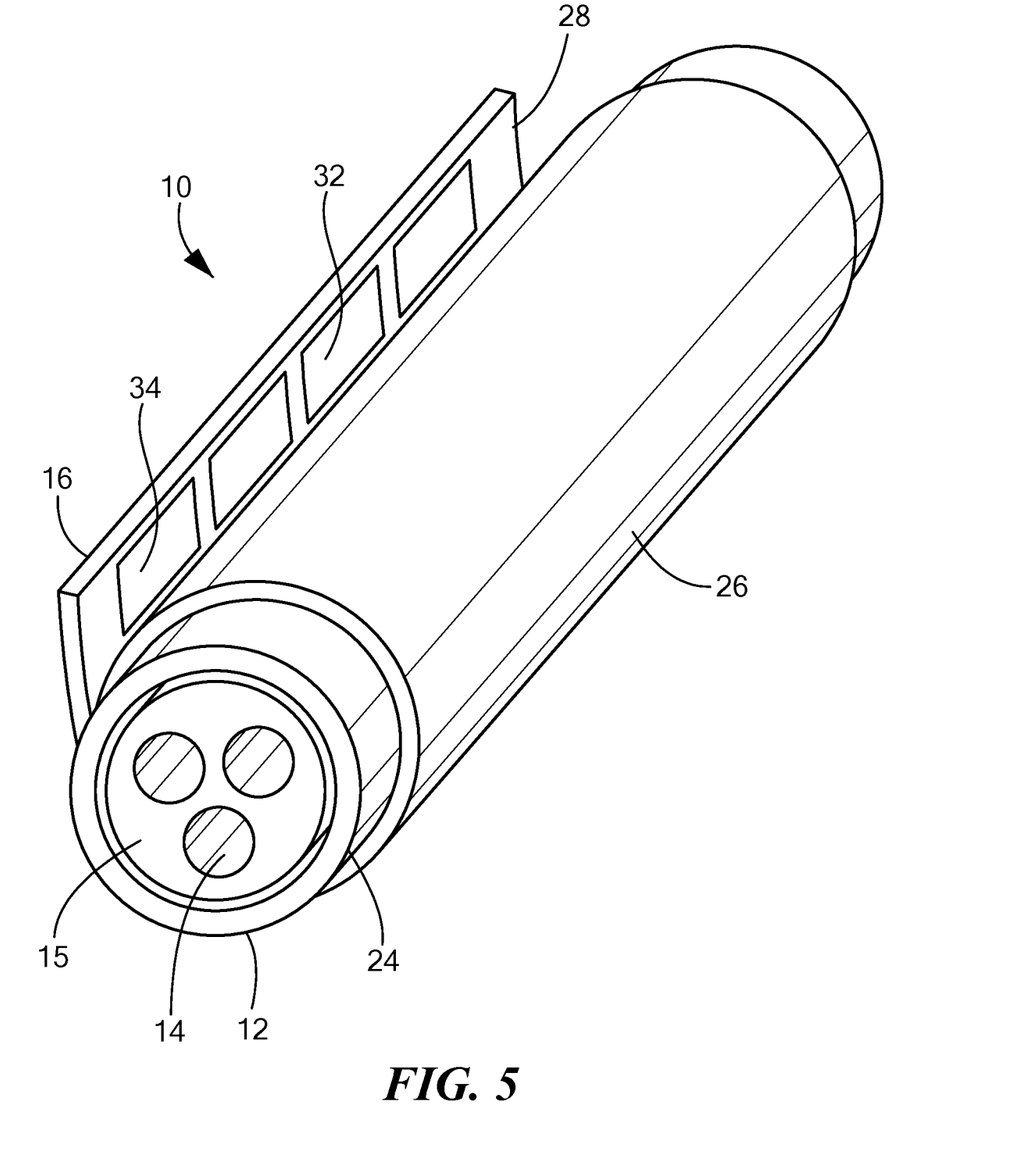
FIG. 5 is a perspective view of the driveline of FIG. 1 showing the electronic instrument as a wireless receiver.

With reference to FIG. 5, the electronic instrument 22 is shown as the wireless transmitter 34 configured to implement a variety of wireless communication protocols. For example, the wireless transmitter 34 and the activity sensors 32 may be coupled to the driveline 10 such that the wireless transmitter 34 communicates the activity information about the patient obtained by the activity sensors 32 to the processor (not shown). As such, the accelerometer 33 of the activity sensor 32 may be in communication with the wireless transmitter 34 to communicated measured patient positional information to the external controller. The activity information and/or patient positional information may be used by a treatment provider to establish or alter a treatment regimen, monitor the patient for safety purposes, or the like.

Figure 6:
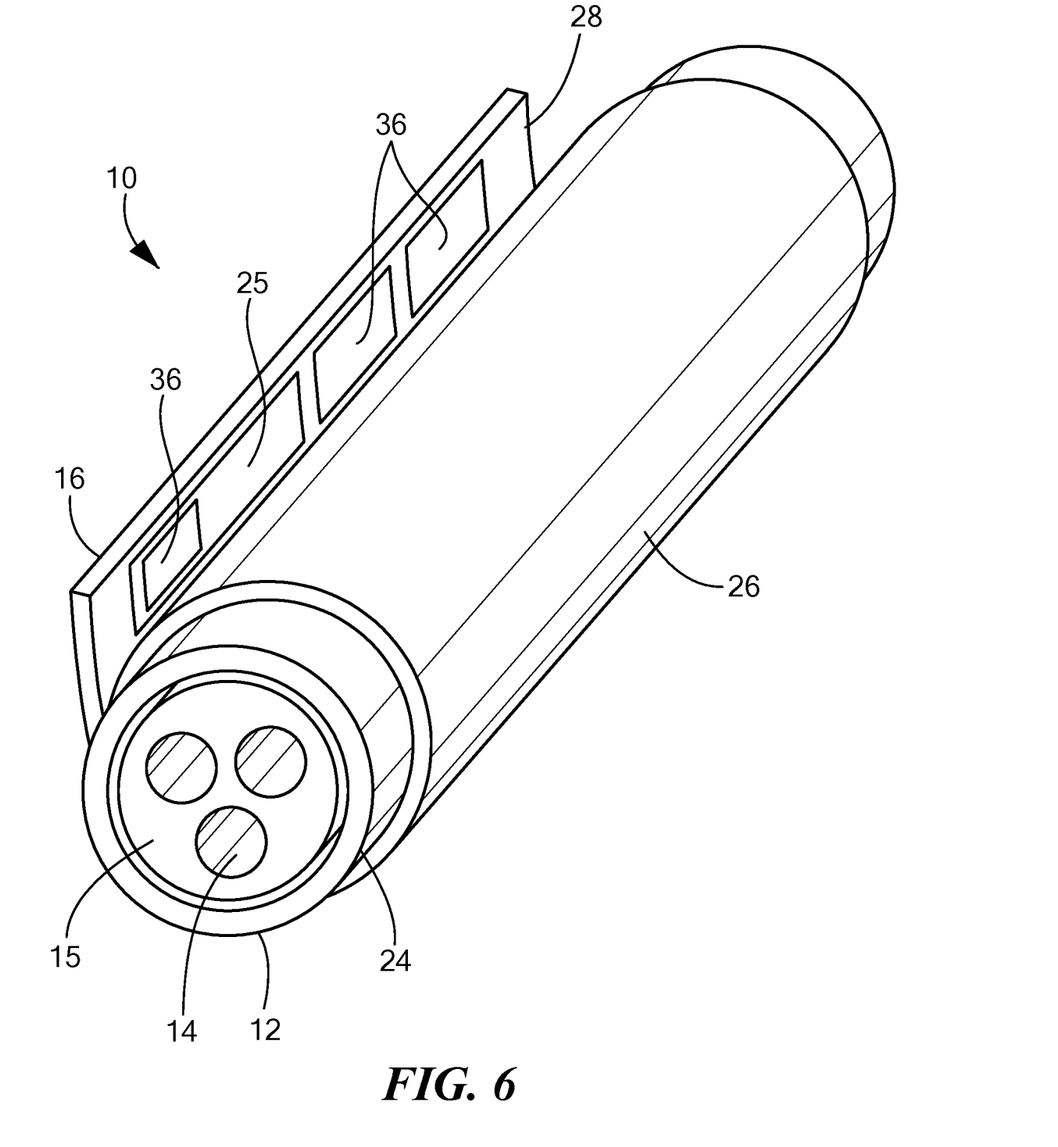
FIG. 6 is a perspective view of the driveline of FIG. 1 showing the electronic instrument as a transcutaneous energy transmitter.

Referring to FIG. 6, the electronic instrument 22 is shown as the transcutaneous energy transfer ("TETS") receiver 36 which may be part of a MEMS device, such as the MEMS device 25. In one configuration, a single TETS receiver 36 may be provided. In another configuration, as shown in FIG. 6, the electronic instrument 22 may by in the form of an array of TETS receivers 36 extending along the entire or less than the entire length of the driveline 10 to provide for a greater surface area for energy transmission.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the disclosure, which is limited only by the following claims.

What is claimed is:

1. A driveline for an implantable blood pump, comprising:
a percutaneous connector including an outer tube, the outer tube defining an exterior surface and having a proximal portion and a distal portion opposite the proximal portion, the proximal portion being couplable to the implantable blood pump adapted to be located within a body of a patient and the distal portion being couplable to an external controller outside of the body of the patient; the exterior surface of the outer tube includes a biocompatible fabric disposed around at least a portion thereof, the biocompatible fabric includes an interior surface and an exterior surface opposite the interior surface, the interior surface configured to be in contact with the exterior surface of the outer tube and to include at least one electronic instrument disposed thereon.

2. The driveline of claim 1, wherein the at least one electronic instrument is at least one from a group consisting of a wireless transmitter and a transcutaneous energy transfer receiver.

3. The driveline of claim 2, wherein the at least one electronic instrument is an activity sensor.

4. The driveline of claim 3, wherein the activity sensor includes an accelerometer in communication with the wireless transmitter, and wherein the wireless transmitter is configured to transmit patient positional information measured by the accelerometer to the external controller.

5. The driveline of claim 4, wherein the external controller is configured to alter an operation of the implantable blood pump based on the patient positional information measured by the accelerometer.

6. The driveline of claim 5, wherein the patient positional information includes a measure of a movement and an orientation of the body of the patient.

7. The driveline of claim 1, wherein the at least one electronic instrument is a moisture sensor.

8. The driveline of claim 1, wherein the outer tube defines a lumen including a plurality of conductors disposed therein.

9. The driveline of Claim 1, wherein the biocompatible fabric is a velour material.

10. The driveline of claim 1, wherein the distal portion of the outer tube extends out from the body of the patient when the connector is implanted in the body of the patient, and the at least one electronic instrument is disposed around the distal portion.

11. The driveline of claim 1, wherein the at least one electronic instrument is adhered to the biocompatible fabric.

12. A driveline for an implantable blood pump defining a communication channel between the implantable blood pump and an external controller, the driveline comprising:
a percutaneous connector including an outer tube, the outer tube defining a proximal portion and a distal portion opposite the proximal portion; and
a biocompatible fabric including an interior surface and an exterior surface opposite the interior surface, the interior surface of the biocompatible fabric being in contact with the outer tube and including an electronic instrument disposed thereon.

13. The driveline of claim 12, wherein the outer tube defines a lumen including a plurality of conductors disposed therein.

14. The driveline of claim 12, wherein the biocompatible fabric is a velour material.

15. The driveline of claim 12, wherein the electronic instrument is adhered to the biocompatible fabric.

16. The driveline of claim 12, wherein the electronic instrument is at least one from a group consisting of a wireless transmitter, a transcutaneous energy transfer receiver, a moisture sensor, and an activity sensor.

17. A driveline for an implantable blood pump, comprising:
a percutaneous connector and an outer tube coupled to the connector, the outer tube including a proximal portion and a distal portion opposite the proximal portion, the proximal portion being adapted to be couplable to the blood pump when implanted within a body of a patient and the distal portion being couplable to an external controller outside of the body of the patient, the outer tube defining a lumen including a plurality of conductors disposed therein and an exterior surface surrounding the lumen;
a biocompatible fabric in contact with the outer tube at the distal portion of the outer tube, the biocompatible fabric including an interior surface and an exterior surface opposite the interior surface; and
at least one electronic instrument disposed between the interior surface of the biocompatible fabric and the exterior surface of the outer tube.

* * * * *